US006442424B1

(12) United States Patent
Ben-Haim et al.

(10) Patent No.: US 6,442,424 B1
(45) Date of Patent: Aug. 27, 2002

(54) LOCAL CARDIAC MOTION CONTROL USING APPLIED ELECTRICAL SIGNALS

(75) Inventors: Shlomo Ben-Haim; Nissim Darvish, both of Haifa; Yuval Mika, S. Zichron Yaakov; Benny Rousso, Bat Yam; Bella Felzen, Haifa; Dov Malonek, Qiryat Tivon, all of (IL)

(73) Assignee: Impulse Dynamics N.V., Curacao (AN)

( * ) Notice: Subject to any disclaimer, the term of this patent is extended or adjusted under 35 U.S.C. 154(b) by 0 days.

(21) Appl. No.: 09/320,090

(22) Filed: May 26, 1999

(51) Int. Cl.[7] .......................... A61N 1/36; A61N 1/362
(52) U.S. Cl. ................................. 607/3; 607/9
(58) Field of Search .......................... 607/4, 5, 14, 15, 607/66, 2, 3, 9

(56) References Cited

U.S. PATENT DOCUMENTS

| | | | | |
|---|---|---|---|---|
| 5,540,722 A | * | 7/1996 | Clare et al. ..................... | 607/5 |
| 5,651,378 A | | 7/1997 | Matheney et al. | |
| 5,814,079 A | * | 9/1998 | Kleival ........................... | 607/4 |
| 5,913,876 A | * | 6/1999 | Taylor et al. ................... | 607/2 |
| 6,266,564 B1 | * | 7/2001 | Hill et al. ....................... | 607/9 |

OTHER PUBLICATIONS

R. A. Malkin and B. K. Hoffmeister; "AC Leakage Curents Cause Complete Hemodynamic Collapse below the Ventricular Fibrillation Threshold"; 1999 Computers in Cardiology Annual Conference, Hannover, Germany, Sep. 1999.

Hayashi et al., "Right Vagal Nerve Stimulation During Minimally Invasive Direct Coronary Artery Bypass Grafting in Dogs. A Preliminary Study", *Journal of Cardiovascular Surgery* (Torino), 39:4, Aug. 1998, pp. 469–471.

C. D. Swerdlow et al., "Cardiovascular collapse caused by electrocardiographically silent 60–Hz intracardiac leakage current: Implications for electrical safety" *Circulation*99(19), pp. 2559–2564; May 18, 1999.

W. R. Burfeind Jr. et al., "The effects of mechanical cardiac stabilization on left ventricular performance", *European Journal of cardio–thoracic Surgery* 14, pp. 285–289, 1998.

R. G. Matheny and C. J. Shaar, "Vagus nerve Stimulation as a method to temporarily slow or arrest the heart". *Annuals of Thoracic Surgery*. 63(6) Supplement, pp. S28–29, Jun. 1997.

\* cited by examiner

*Primary Examiner*—Carl Layno
(74) *Attorney, Agent, or Firm*—Cowan, Liebowitz & Latman, P.C.; William H. Dippert

(57) ABSTRACT

A method and apparatus for performing a medical procedure on a beating heart. Electrical signals are applied to the heart so as to reduce motion of a segment thereof, and the procedure is performed while the heart continues to pump blood. Preferably, the motion increases spontaneously after the signals are removed.

15 Claims, 4 Drawing Sheets

LOCAL CARDIAC MOTION CONTROL USING APPLIED ELECTRICAL SIGNALS

FIELD OF THE INVENTION

The present invention relates generally to invasive devices and methods for treatment of the heart, and specifically to devices and methods for controlling the heart muscle during surgery.

BACKGROUND OF THE INVENTION

Heart surgery is often accompanied by the induction of cardioplegia (elective stopping of essentially all cardiac activity by injection of chemicals, selective hypothermia, mechanical stabilization, or electrical stimuli). In humans, induced global cardioplegia is nearly always practiced in conjunction with cardiopulmonary bypass.

Recently, minimally-invasive methods of cardiac surgery have been developed, in which the heart is approached through an incision made between the ribs, without sternotomy. It is sometimes preferred that, rather than inducing cardioplegia, the surgeon mechanically restrains a portion of the heart on which a surgical procedure, such as a bypass graft, is to be performed. Various tools and methods have been developed for this purpose, such as: (a) a suction cup-based stabilization platform (e.g., the Utrecht Octopus); (b) mechanical stabilization devices, such as the CTS Access Ultima System, produced by Cardiothoracic System, Cupertino, Calif.; (c) the Octopus 2 or the EndoOctopus device, both produced by Medtronic, Minneapolis, Minn.; (d) a U-shaped metal foot and other stabilizers produced by Genzyme Surgical Products, Tucker, Ga.; (e) the Octopus Suction stabilizer, produced by fedtronic GmbH, Germany; and (f) CardioVations mechanical stabilizers produced by Ethicon Endo-Surgery, Cincinnati, Ohio.

Such mechanical restraint of the heart muscle requires that substantial force, e.g., pressure or vacuum, be applied, which can cause tissue trauma; and the implements involved interfere with the surgeon's work. This interference typically includes reducing the surgeon's free workspace and limiting the extent of tissue stabilization, due to concerns about tissue injury. Other effects of mechanical stabilization are described in an article, "The effects of mechanical stabilization on left ventricular performance," by Burfeind et al., *European Journal of Cardio-Thoracic Surgery*, 14 (1998), pp. 285–289, which is incorporated herein by reference,.

PCT patent application PCT/IL97/00012, published as Wo 97/25098, to Ben-Haim et al., which is incorporated herein by reference, describes methods for modifying the force of contraction of at least a portion of a heart chamber by applying a non-excitatory electrical signal to the heart at a delay after electrical activation of the portion. The signal may be applied in combination with a pacemaker or defibrillator, which also applies an excitatory signal (i.e., pacing or defibrillation pulses) to the heart muscle.

PCT patent application PCT/IL97/00236, which is also incorporated herein by reference, describes a pacemaker that modifies cardiac output. This pacemaker applies both excitatory (pacing) and non-excitatory electrical signals to the heart. By applying non-excitatory signals of suitable strength, appropriately timed with respect to the heart's electrical activation, the contraction of selected segments of the heart muscle can be increased or decreased.

U.S. Pat. No. 5,651,378, to Matheny et al., and an article entitled, "Vagus Nerve Stimulation as a Method to Temporarily Slow or Arrest the Heart," by Matheny and Shaar, *Annals of Thoracic Surgery*, 63 (6) Supplement (June 1997), pp. S28–29, which are both incorporated herein by reference, describe a method to stimulate the vagus nerve in order to slow or stop a patient's heart during coronary artery bypass grafting surgery. While these methods describe electrically-stimulating the vagus nerve, their operation is, overall, substantially similar to chemical means of inducing cardioplegia, and are therefore characterized by a generally slow time constant following application and removal of the vagal nerve stimulation.

SUMMARY OF THE INVENTION

It is an object of some aspects of the present invention to provide improved methods and apparatus for regulating motion of the heart.

It is a further object of some aspects of the present invention to provide improved methods and apparatus for reducing motion of the heart during minimally-invasive and open-chest surgery.

In preferred embodiments of the present invention, an electrical cardiac stimulator allows a patient's heart to pump blood while inhibiting motion of a segment of the heart. The stimulator comprises one or more electrodes, preferably placed at multiple sites in or on the heart, and a control unit. The control unit administers electrical signals to at least one of the electrodes in order to reduce or substantially stop motion of the segment for the duration of signal application. Termination of signal application allows the segment, as well as the heart as a whole, to resume normal motion. Preferably, the reduction in motion of the segment, as provided by the present invention, is used to enable a surgeon to perform minimally-invasive surgery or open-chest surgery, generally without inducing global cardioplegia or requiring cardiopulmonary bypass.

In some preferred embodiments of the present invention, administration of the electrical signals is accompanied by use of a stabilizer, typically a mechanical stabilizer, in conjunction with the electrical signals to further reduce motion of the segment. Similarly, for some applications, electrical signals as provided by embodiments of the present invention are used to reduce the force applied—and thus the injury produced—by a stabilizer, while maintaining a desired level of motion reduction.

In some preferred embodiments of the present invention, one or more motion sensors, e.g., accelerometers, are coupled to the heart, and send motion signals to the control unit indicative of the segment's motion and, optionally, of the motion of other areas of the heart. Preferably, the motion signals serve as feedback to enable the control unit to adjust the electrical signals applied to the heart, in order to reduce the detected motion of the segment. In a preferred embodiment, one of the motion sensors is coupled to the segment of the heart, adjacent to a surgical location within the segment, and is in a vicinity of at least one motion-reduction electrode. The control unit receives motion signals from the sensor, and actuates the motion-reduction electrode to apply the electrical signals, referred to herein as "motion-reduction pulses," in order to change contractility and contraction timing of muscle in the segment.

The motion-reduction pulses preferably comprise one or more of: regular pacing pulses, rapid pacing pulses, a fencing signal, and an enhancement signal. The enhancement signal is typically similar to signals used for Excitable Tissue Control, as described in U.S. Pat. application Ser. No. 09/260,369, which is assigned to the assignee of the present patent application and incorporated herein by reference.

Most preferably, the motion-reduction pulses are synchronized with the overall heartbeat, and have timing, shape, and magnitude characteristics which are determined during a calibration period of the control unit. During the calibration period, a high degree of stabilization is preferably achieved, while maintaining adequate safety margins, e.g., acceptable standard patient vital signs, and avoidance of fibrillation and arrhythmia.

Generally, motion of the segment is characterized by a sum of: (a) a first component, consisting of motion resulting from general contraction and relaxation of the heart, which may depend on parameters of stimulation applied through the one or more motion-reduction electrodes and the contraction force generated thereby; and (b) a second component, consisting of local motion resulting from that part of the heart which is substantially stimulated by the motion-reduction electrodes. It is a goal of this embodiment of the present invention to apply motion-reduction pulses which alter the motion of the first and second components, particularly with respect to the timing thereof, such that the net motion of the segment, resulting from summing the two components, is generally minimized and/or smoothed.

In some of the embodiments in which a mechanical stabilizer is used in conjunction with the applied signals, the control unit typically places a greater emphasis on reducing the second component than on reducing the first component. It is believed that mechanical stabilizers are generally more successful in reducing the global component of the heart's motion which is transferred to a local region of the heart than in reducing movements generated within the local region.

In some preferred embodiments of the present invention, the electrodes are placed at multiple sites on the epicardium and/or endocardium of the segment of the heart. Alternatively or additionally, the electrodes are placed in blood vessels of the heart or in a vicinity of the heart, and, optionally, on areas of the heart other than the segment. Typically, each electrode conveys a particular waveform to the heart, which may differ in certain aspects from the waveforms applied to other electrodes. The particular waveform to be applied to each electrode is preferably determined by the unit under the control or supervision of a human operator, in such a manner as to minimize the motion of the segment.

A U.S. patent application filed on even date, entitled, "Induction of cardioplegia using applied electrical signals," which is assigned to the assignee of the present invention and is incorporated herein by reference, describes methods for applying electrical signals to the heart to induce a global cardioplegic state. Aspects of such methods may also be used in conjunction with the principles of the present patent application. In a preferred embodiment of the present invention, the electrical signals applied to the heart comprise rapid pacing pulses and/or fencing signals, as described hereinbelow, applied through one or more of the electrodes placed on or in a vicinity of the segment, in order to induce a state of generally constant and/or reduced contraction of the segment for a predetermined time period. The use of such pulses is described further in the above-mentioned application regarding induction of cardioplegia. Additionally, the signals may be applied to other regions of the heart in order to modify contraction parameters in the other regions (e.g., timing and strength), such that motion of the segment is reduced.

In some preferred embodiments of the present invention, a "fencing" signal is applied through one or more of the electrodes, preferably in order to prevent or inhibit the propagation of an action potential from one region of the heart to another. Fencing may be applied in conjunction with any (or none) of the motion-reduction pulses described hereinabove. Most preferably, the fencing signal is applied in a vicinity of the segment. Such fencing is described in U.S. patent application Ser. No. 09/254,903, which is assigned to the assignee of the present patent application and incorporated herein by reference. Fencing is typically used, according to these embodiments, to reduce a motion and/or a contraction force of the segment, generally by blocking or reducing the normal propagation of signals, and sometimes by applying the fencing signal to one or more sites within the segment.

In some preferred embodiments of the present invention, periods of electrical signal application are separated by signal non-application periods. Preferably, the durations of the application and non-application periods are set to maximize the surgeon's time for performing surgery, while continuing to generally assure that the patient's systemic oxygen needs are satisfied.

For some applications, it may be desirable to partially (and, in some cases, significantly) reduce the overall output of the heart in order to attain a high degree of stabilization of the segment for a short time. Suitable methods of electrical control of the heart to reduce cardiac output are described in the above-mentioned PCT patent applications PCT/IL97/00012 and PCT/IL97/00236, for example, and in the corresponding U.S. national phase patent applications, Ser. Nos. 09/101,723 and 09/254,900, which are assigned to the assignee of the present patent application and incorporated herein by reference. It is emphasized that in these embodiments, as in most applications of the present invention, the patient's vital signs are preferably monitored substantially continuously.

In some preferred embodiments of the present invention, an automatic or operator-assisted feedback loop is used in order to optimize the level of stabilization, without undesirably changing measured physiological parameters, such as, for example, pCO2, pO2, Left Ventricular Pressure (LVP), ECG, and systemic blood pressure. Preferably, an abnormal value of any of these parameters triggers an alarm, responsive to which the operator and/or the control unit initiates an appropriate response. Further preferably, arrhythmia and fibrillation detection capabilities, as well as appropriate treatment protocols, are incorporated into the control unit.

Preferably, application of the electrical signals in accordance with the present invention stabilizes the segment within a very short period, typically about 1 second, and can maintain the segment's stability for prolonged periods. The heart typically returns to normal function within about 2 seconds of removal of the electrical signals.

There is therefore provided, in accordance with a preferred embodiment of the present invention, a method for performing a medical procedure on a beating heart, including:

applying electrical signals to the heart so as to reduce motion of a segment thereof; and performing the procedure while the heart continues to pump blood.

Preferably, applying the signals includes modifying contraction of muscle tissue of the heart, wherein modifying the contraction includes inducing contraction of the muscle tissue.

Further preferably, applying the signals includes:

determining an aspect of the motion of the segment due generally to contraction of muscle tissue outside the segment; and adjusting the signals so as to reduce the aspect of the motion of the segment.

Preferably, applying the signals includes applying pulses at a rate greater than 5 Hz, and most preferably greater than 10 Hz.

In a preferred embodiment, the method includes mechanically stabilizing the segment in conjunction with applying the electrical signals.

Preferably, applying the electrical signals includes applying bipolar signals or, alternatively or additionally, unipolar signals.

Preferably, applying the electrical signals includes calibrating the signals intermittently during the procedure.

In a preferred embodiment, applying the electrical signals includes applying a first signal so as to precondition a response of the heart to a subsequent signal, which reduces the motion during the procedure.

Preferably, performing the procedure includes performing a treatment on the segment.

Further preferably, applying the signals includes:
intermittently applying the signals, to reduce motion of the segment; and
intermittently removing the signals, to enable the heart to pump blood regularly.

In a preferred embodiment, applying the signals includes:
sensing electrical activity of the heart to detect arrhythmia thereof; and
applying electrical energy to the heart to treat the arrhythmia.

In a preferred embodiment, the method includes performing thoracic surgery while motion of the segment is reduced.

Alternatively, the method includes performing a diagnostic procedure while motion of the segment is reduced.

Preferably, the method includes, sensing motion of the heart, wherein applying the signals includes modifying a characteristic of at least some of the signals applied to the heart responsive to the sensed motion. Most preferably, sensing the motion includes coupling at least one motion sensor to detect motion of the segment of the heart, wherein modifying the characteristic includes modifying a signal characteristic so as to reduce the motion of the segment.

In a preferred embodiment, applying the signals includes applying a fencing signal to the heart to block propagation of an activation wave into the segment of the heart. Alternatively or additionally, applying the signals includes applying a fencing signal in a vicinity of the segment to reduce a contraction force thereof.

Preferably, applying the electrical signals includes applying signals, most preferably including pacing signals, at a plurality of sites on the heart. Most preferably, applying the signals includes applying a first waveform at a first one of the sites and applying a second waveform, which differs from the first waveform, at a second one of the sites, wherein applying the first and second waveforms includes controlling a timing relationship of the waveforms so as to reduce the motion of the segment.

There is also provided, in accordance with a preferred embodiment of the present invention, apparatus for performing a medical procedure on a beating heart, including:
one or more electrodes, coupled to the heart; and
a control unit, which actuates the electrodes to apply electrical signals to the heart so as to substantially reduce motion of a segment thereof while the heart continues to pump blood, whereby the procedure is performed on the segment.

Preferably, the signals cause contraction of muscle tissue of the heart.

Preferably, the electrodes include one or more local sense electrodes, coupled to the heart and to the control unit, which sense electrical activity of the heart to detect arrhythmia thereof, and convey a signal responsive to the sensing to the control unit.

Further preferably, the apparatus includes one or more motion sensors, coupled to the heart and to the control unit, which sense motion of the heart, wherein the control unit modifies the signals applied to the heart responsive to the motion. Most preferably, at least one of the one or more motion sensors is coupled to the segment of the heart, and the control unit modifies the signals so as to minimize motion sensed by the at least one sensor.

In a preferred embodiment, the apparatus includes one or more fencing electrodes, coupled to the heart, which are actuated by the control unit to apply a fencing signal to the heart so as to block propagation of an activation wave into the segment. Alternatively or additionally, the one or more fencing electrodes are actuated by the control unit to apply a fencing signal to the segment so as to reduce a contraction force thereof.

In another preferred embodiment, the apparatus includes a mechanical stabilizer, which is applied to the heart to restrain motion thereof, in conjunction with motion reduction using the one or more electrodes.

There is further provided, in accordance with a preferred embodiment of the present invention, a method for performing a medical procedure on muscle tissue having a tendency to motion, including:
applying electrical signals to the tissue so as to reduce motion of a segment thereof, such that the motion increases spontaneously upon removal of the signals; and
performing the procedure while the motion is reduced.

Preferably, the muscle tissue includes heart tissue or, alternatively or additionally, smooth muscle or skeletal muscle.

Preferably, performing the procedure includes performing a diagnostic procedure or, alternatively or additionally, a therapeutic procedure.

There is moreover provided, in accordance with a preferred embodiment of the present invention, apparatus for performing a medical procedure on muscle tissue having a tendency to motion, including:
one or more electrodes, coupled to the tissue; and
a control unit, which actuates the electrodes to apply electrical signals to the tissue so as to reduce motion of a segment thereof, whereby the procedure is performed on the segment, and such that the motion increases spontaneously upon removal of the signals.

The present invention will be more fully understood from the following detailed description of the preferred embodiments thereof, taken together with the drawings, in which:

DETAILED DESCRIPTION OF PREFERRED EMBODIMENTS

Figure 1:
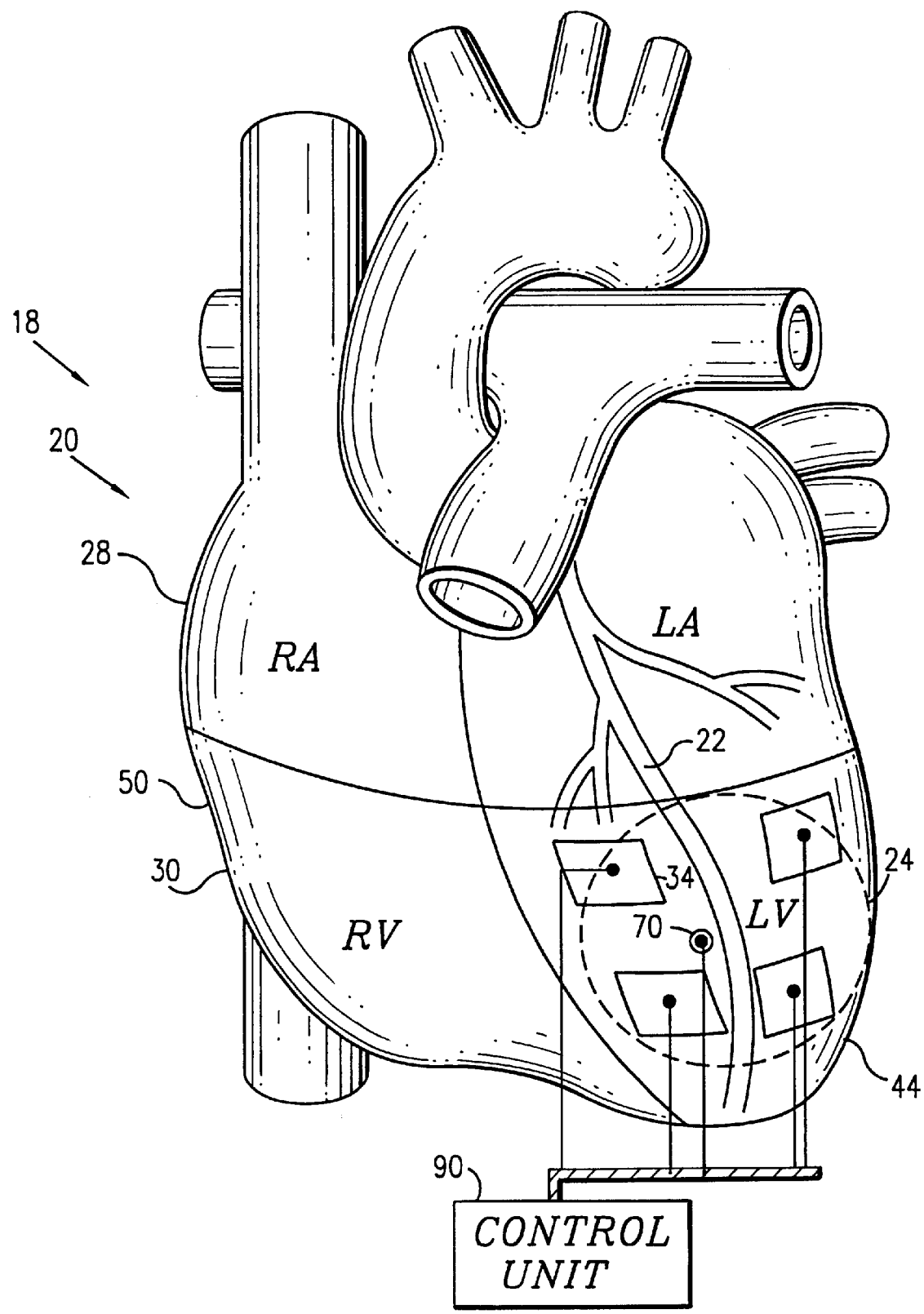
FIG. 1 is a schematic illustration of the external surface of a heart, showing the placement of patch electrodes on a ventricle thereof, in accordance with a preferred embodiment of the present invention.

FIG. 1 is a schematic illustration of apparatus 18 for reducing the motion of a segment 24 of a patient's heart 20, in order to enable surgery within the segment, in accordance with a preferred embodiment of the present invention. One or more patch electrodes 34 are preferably coupled to the epicardium 50 overlying left ventricle 44, within segment 24 or in a vicinity thereof. Additionally, an optional motion sensor 70 (e.g., an accelerometer) is coupled to the heart, preferably adjacent to a surgical location within segment 24. A control unit 90, preferably coupled to electrodes 34 and to sensor 70, is used to reduce motion of the segment during cardiac surgery, typically by applying electrical signals to the electrodes responsive to motion signals generated by the motion sensor, as described further hereinbelow.

Figure 2:
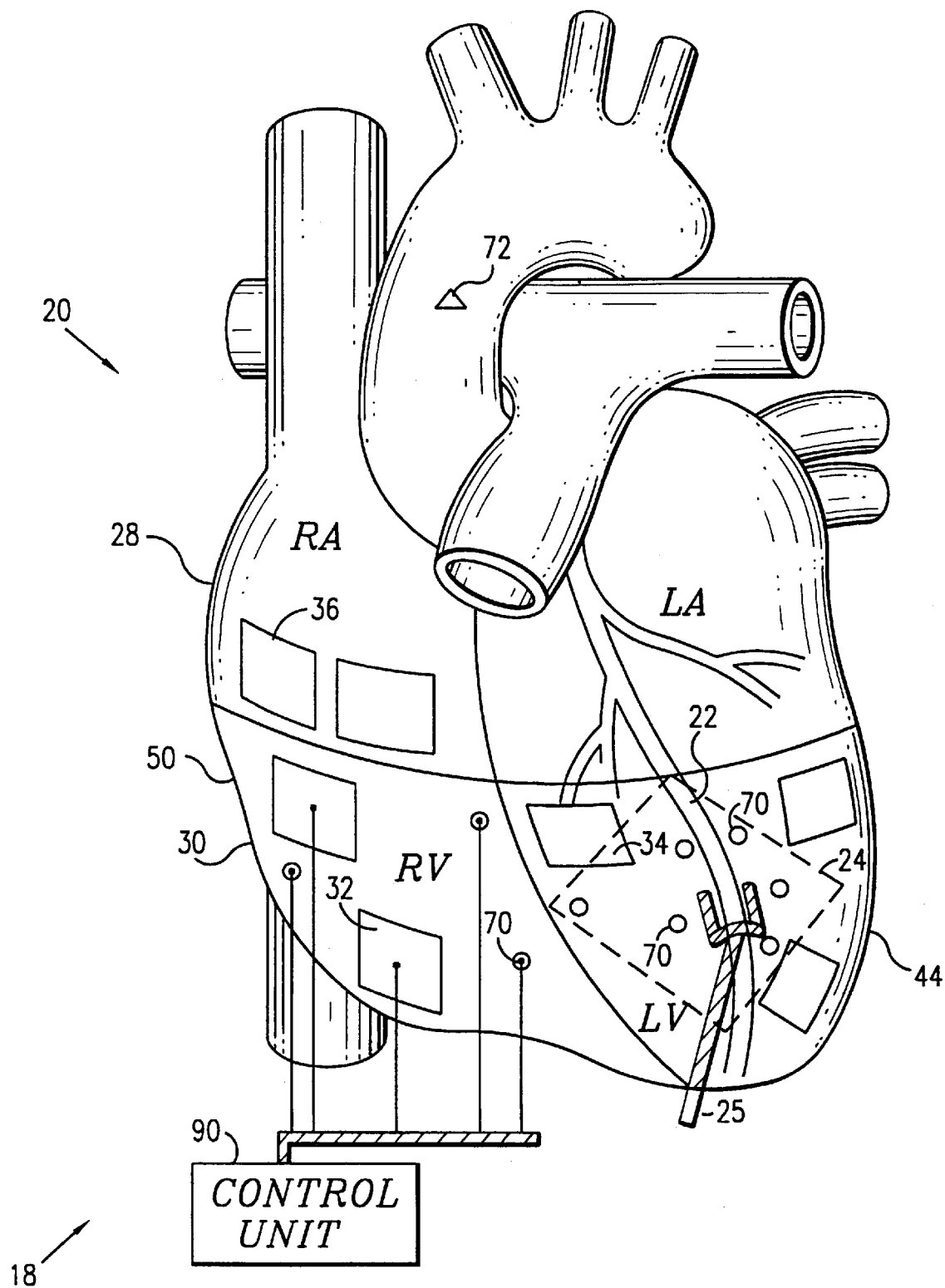
FIG. 2 is a schematic illustration of the external surface of a heart, showing the placement of patch electrodes on multiple chambers thereof, in accordance with another preferred embodiment of the present invention.

FIG. 2 is a schematic illustration of apparatus 18, comprising a greater number of electrodes and sensors than in the embodiment shown in FIG. 1, in accordance with another preferred embodiment of the present invention. One or more patch electrodes 32, 34, and 36 are coupled to the epicardium 50 overlying, respectively, the right and left ventricles 30 and 44 and right atrium 28 of heart 20. Additionally, a plurality of motion sensors 70 and one or more optional supplemental sensors 72 (e.g., systemic blood pressure, LVP, pO2, pCO2, ECG, and flow rate sensors) are coupled to the heart or placed elsewhere on or in the patient's body. Control unit 90 is preferably coupled to all of the electrodes and sensors, but for clarity, connections between the control unit and only some of the electrodes and sensors are shown in FIG. 2. The electrodes and sensors provide substantially continuous monitoring of the patient's vital signs, in order to ensure that all of the signs are maintained within a safe range during the surgery. To the extent that any of the vital signs is outside the range, control unit 90 will either take corrective action on its own and/or provide an alarm to the surgeon, who will then be able to take the required action.

In some applications, a stabilization element 25 applies a mechanical force to segment 24 in order to reduce the motion thereof. The force may include positive pressure and/or vacuum. Typically, application of signals as provided by embodiments of the present invention enables the mechanical force applied by element 25 to be reduced, in order to minimize or eliminate injury produced thereby. Additionally, use of element 25 in conjunction with the signals may reduce motion of the segment to a level below that which could be attained by applying the element or the signals separately. The contact surface between element 25 and the heart may comprise electrodes (not shown) which sense and/or apply energy to the heart, using methods described herein.

Figure 3:
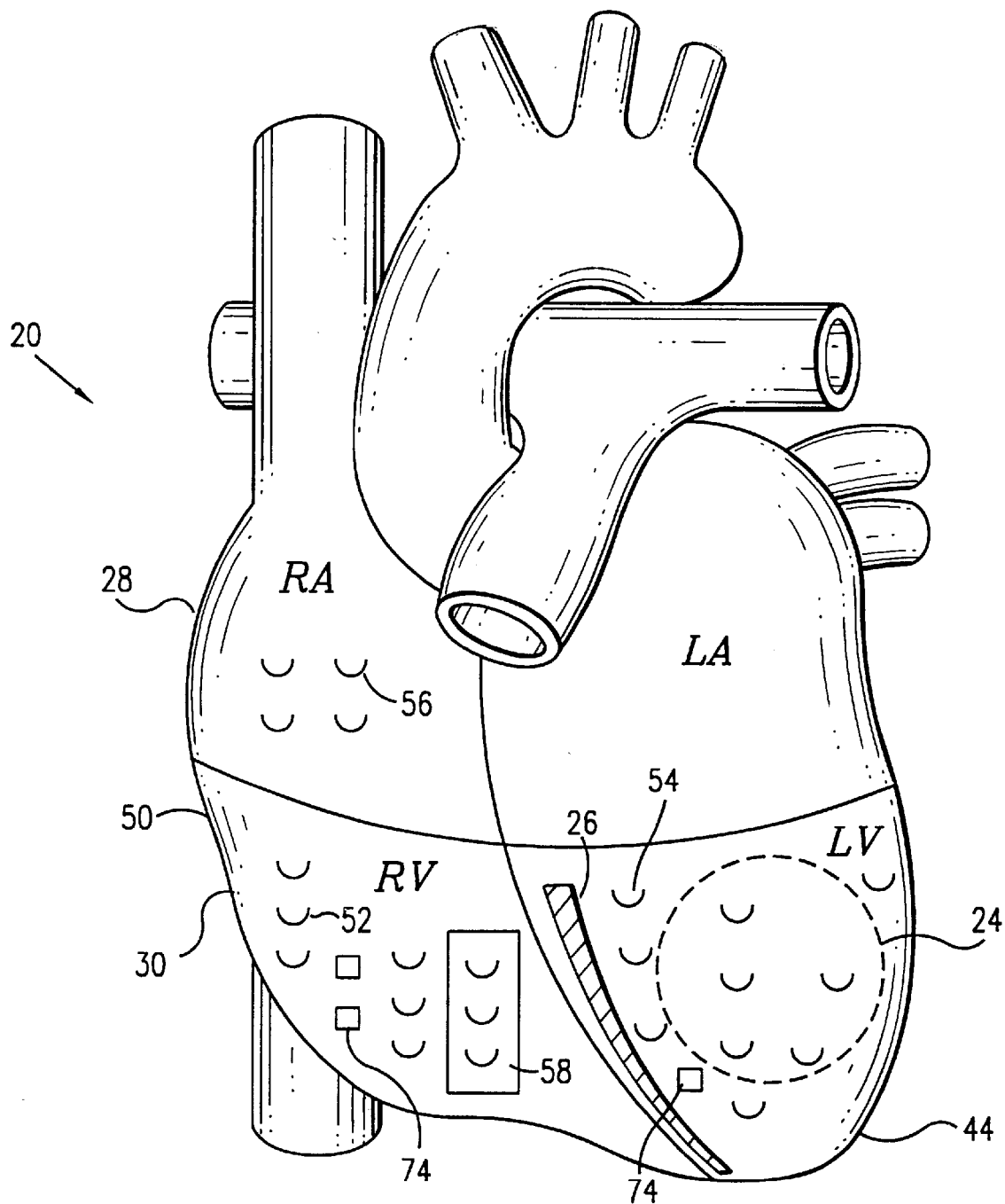
FIG. 3 is a schematic illustration of the external surface of a heart, showing the placement of needle electrodes therein, in accordance with yet another preferred embodiment of the present invention.

FIG. 3 is a schematic illustration showing the placement of one or more needle and/or wire electrodes 52, 54, and 56 onto epicardium 50, over chambers 30, 44 and 28, respectively, in accordance with yet another preferred embodiment of the present invention. Some of the needle and/or wire electrodes are optionally coupled to strips 58, which are themselves coupled to heart 20. Local sense electrodes 74 are preferably coupled to the epicardium or placed within one or more chambers of the heart, and convey electrical signals responsive to cardiac electric activity to circuitry of control unit 90 (not shown in this figure). Alternatively or additionally, needle or wire electrodes 52, 54, and 56 may be used for local sensing, as well as stimulation. An optional strip 26 comprising electrodes may be coupled to the heart in a vicinity of segment 24, for the surgeon's convenience.

The types and placement of electrodes and sensors in FIGS. 1–3 are shown by way of example. Other sites in and around the heart are appropriate for electrode or sensor placement in other applications of the present invention. Additionally, different numbers of electrodes or sensors (including no electrodes or sensors in some areas) and different types and combinations of sensors and coil, defibrillation, basket, screw, patch, needle and wire electrodes may be used in applying the principles of the present invention.

Figure 4:
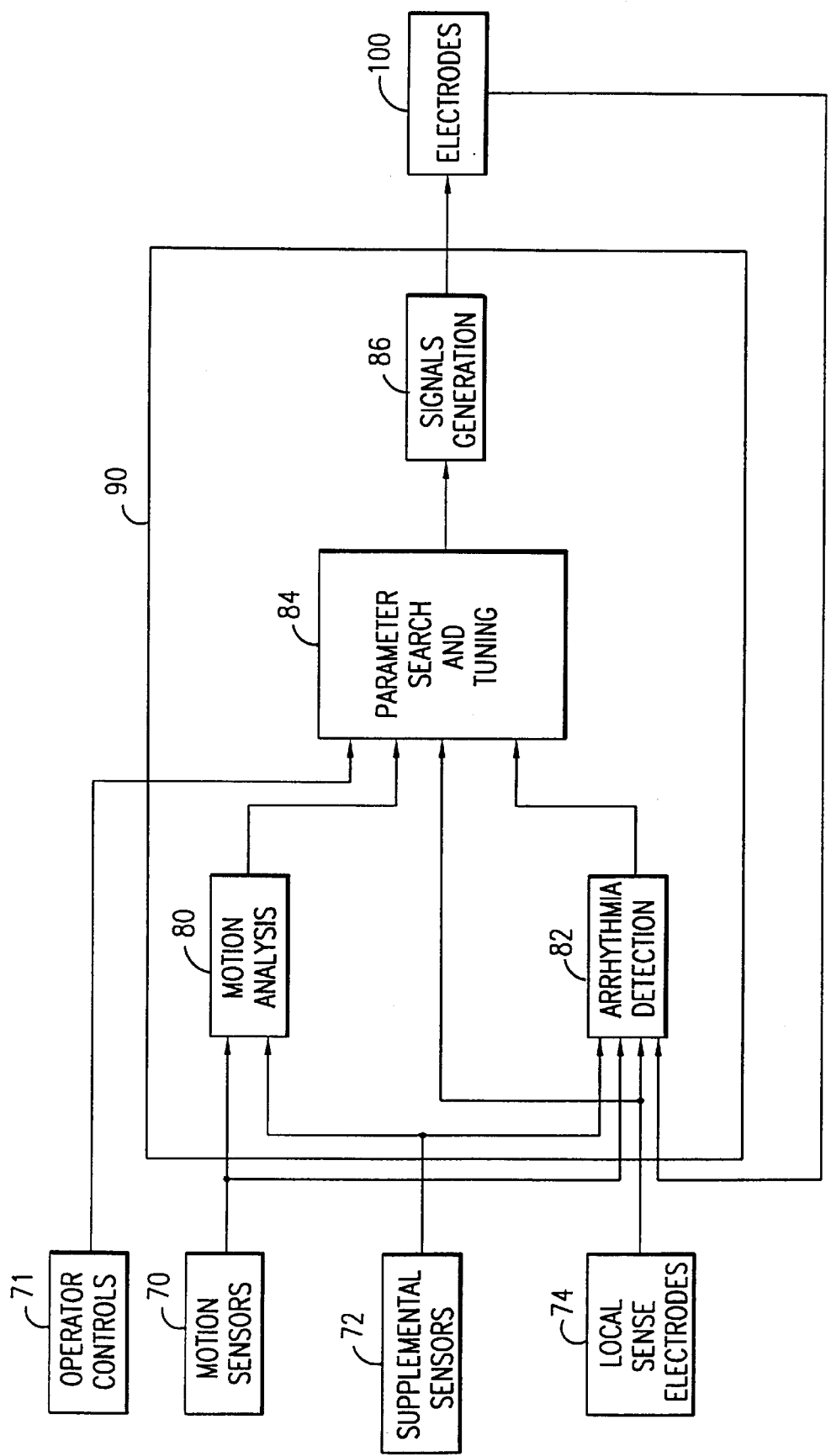
FIG. 4 is a schematic block diagram of a control unit, which generates signals to be applied to the electrodes shown in the preceding figures, in accordance with a preferred embodiment of the present invention.

FIG. 4 is a schematic block diagram of control unit 90, which conveys electrical energy to electrodes 100 coupled to heart 20 in order to reduce motion of segment 24, in accordance with a preferred embodiment of the present invention. Typically, electrodes 100 comprise one or more of electrodes 32, 34, 36, 52, 54, 56, and the electrodes of strip 26. Preferably, control unit 90 conveys electrical energy to one or more of electrodes 100, in order to reduce or substantially stop motion of segment 24, and subsequently terminates application of the energy to enable the segment to move and the heart to resume normal beating.

In some operational modes, control unit 90 is operated to intermittently reduce motion of segment 24, by repeated application and removal of the electrical energy. Use of the apparatus in this manner enables a surgeon to perform minimally-invasive surgery or open-chest surgery on the heart, generally without the induction of cardioplegia and without the need for cardiopulmonary bypass. Typically, in minimally-invasive surgery, control unit 90 is coupled to fewer electrodes and sensors (e.g., as in FIG. 1) than in open-chest surgery, wherein a greater number of electrodes and sensors can easily be placed on the heart (e.g., as in FIGS. 2 and 3). Furthermore, for some applications, it is desirable to use trans-venous or trans-arterial electrodes (not shown), typically inserted by catheters into blood vessels of or in a vicinity of the heart, which apply electrical energy through the vessel wall to selected areas of the heart. It is noted that whereas specific types and placements of electrodes are described herein and shown in the figures, it is within the scope of the present invention to use, as appropriate, substantially any electrodes known in the art of tissue stimulation and bioelectrical sensing, and to place these electrodes at one or more locations on or in a vicinity of the heart or elsewhere on or in the patient's body.

Motion sensors 70, described hereinabove with reference to FIGS. 1–3, are preferably coupled to segment 24 or to other locations on heart 20, and send motion sensor signals to a motion analysis unit 80 of control unit 90. The motion sensor signals provide feedback to the control unit, which modifies the electrical energy applied to the heart responsive thereto. Preferably, the electrical energy comprises electrical signals, most preferably including pulses, which are adjusted by the control unit responsive to the motion sensor signals in order to minimize motion of segment 24. Sensors 70 typically comprise one or more accelerometers. For example, one of the accelerometers may include a piezoelectric crystal, which produces an electric field responsive to deformation. Motion analysis unit 80 preferably comprises amplifiers to amplify low-level signals generated by motion sensors 70, and a signal processing unit, coupled to the amplifiers, which determines respective states of motion of the accelerometers. In some applications, motion analysis unit 80 additionally receives signals from one or more of supplemental sensors 72, particularly those sensors that detect mechanical phenomena such as blood flow rate and blood pressure.

Preferably, motion analysis unit 80 conveys results of its analysis to a "parameter search and tuning" block 84 of control unit 90, which iteratively modifies characteristics of the electrical signals in order to reduce the motion of segment 24. To achieve this goal, block 84 typically utilizes multivariate optimization and control methods known in the art (e.g., downhill simplex, linear state variable feedback or extended Kalman filters), in order to cause the measured motion and/or other parameters to converge to a desired value. For the purposes of some embodiments of the present invention, block 84 typically modifies a set of controllable parameters to minimize and/or smooth motion of segment 24. Preferably, the controllable parameters are conveyed by block 84 to a signals generation block 86 of control unit 90, which generates, responsive to the parameters, electrical signals that are applied by electrodes 100 to the various sites on heart 20. Examples of methods used by control unit 90 to reduce the motion of segment 24 in the embodiments shown in FIGS. 1–3 are described hereinbelow.

Reference is now made to FIGS. 1 and 4. Typically, motion sensor 70 is coupled to segment 24, adjacent to a surgical location within the segment, and is near one or more of electrodes 34. In the embodiment shown in FIG. 1, sensor 70 is placed on the surface of left ventricle 44, adjacent to the left anterior descending artery 22, to enable, for example, a minimally-invasive, single-vessel coronary artery bypass graft (CABG) to be performed thereon. Preferably, the control unit receives motion signals from sensor 70, and actuates electrodes 34 to apply motion-reduction pulses, in order to cause muscle in the segment to contract in a manner which generally reduces motion of the segment, as described hereinbelow.

Most preferably, the motion-reduction pulses have some similarity to pacing pulses and/or are timed to correlate with pacing pulses. They are typically synchronized with the overall heartbeat, and have timing, shape, and magnitude characteristics which are determined during a calibration period at the beginning of a surgical procedure and/or at regular intervals during the procedure. The electrical signals applied to the heart may comprise combinations of signals described herein, including regular pacing, rapid pacing, fencing, enhancement signals and other signals.

Generally, motion of segment 24 is characterized by a sum of: (a) a first component, consisting of global heart motion resulting from beating of heart 20, and especially motion due to contraction of heart regions not within segment 24; and (b) a second component, consisting of motion resulting from the part of the heart in segment 24 that is typically stimulated by electrodes 34. Control unit 90 preferably applies the motion-reduction pulses to segment 24 to alter the second component of the motion, and applies other signals to the rest of the heart to alter the first component (and particularly timing of the first component), such that the net motion of segment 24, resulting from summing the two components, is generally minimized and/or smoothed.

During the calibration period, "parameter search and tuning" block 84 preferably executes an optimization algorithm, such as "gradient descent," in which, for example, block 84 modifies a characteristic (e.g., timing, duration, or magnitude) of the pulses generated by one of the electrodes 34, and then determines whether the measured motion of segment 24 decreases, or changes in some other desired way, following the modification. Typically, in a series of similar calibration steps, block 64 modifies the characteristics of the pulses at the other electrodes, wherein those modifications that reduce motion of segment 24 are generally maintained, and modifications that increase the motion of the segment are eliminated or avoided. In this manner, motion of segment 24 is gradually reduced to a point at which the surgeon can safely and conveniently perform the surgical procedure near sensor 70. Unlike methods known in the art, there is no need for the surgeon to interfere mechanically with the heart motion (although this may be desirable in some cases, as described hereinabove).

In some cases, it is desirable to have a preconditioning period of the segment of the heart and/or of the whole heart. During the preconditioning, the heart is exposed to motion-reduction signals, as provided by some preferred embodiments of the present invention, for short periods initially, followed by progressively longer periods of signals. It has been found that during the preconditioning period, characteristics of the heart s response to the motion-reduction signals change, so that substantially similar inputs will give different responses before and after the preconditioning period. Therefore, for example, during the preconditioning period, the control unit may apply signals for a 2 second period, followed by 4 second, 6 seconds and longer periods, until a desired motion-reduction period of 20 seconds is attained. It is believed that the heart is preconditioned, or "trained," during this period, and that training the heart during the preconditioning period may improve the response of the heart during subsequent signal-application periods. Because the heart may change its response to the applied signals throughout the surgical procedure, i.e., it is continually being trained, it is generally preferable to repeat the calibration at intermittent times during the procedure.

Most preferably, during the calibration period and during regular operation of control unit 90, an arrhythmia detection unit 82 of control unit 90 receives inputs from motion sensor 70, supplemental sensors 72, electrodes 34, and/or other electrodes and sensors (not shown), and evaluates these inputs to detect an onset of cardiac arrhythmia. Preferably, unit 82 employs techniques known in the art for determining arrhythmia, so that control unit 90 can treat or terminate the arrhythmia by pacing or by performing cardioversion or defibrillation. In a preferred embodiment, control unit 90 applies a shockless defibrillation technique, as described in a U.S. Provisional Patent Application, filed on even date, entitled "Shockless defibrillation," which is assigned to the assignee of the present patent application and incorporated herein by reference.

Reference is now made to FIGS. 2, 3, and 4. Preferably, motion sensors 70 (not shown in FIG. 3) send motion sensor signals to control unit 90 indicative of motion of segment 24 and of other areas of heart 20. Typically, the larger numbers of electrodes and sensors shown in the embodiments of FIGS. 2 and 3 are desirable for enhanced control and/or for more complex, often open-chest, operations (e.g., multi-vessel CABG), in which a greater area of the heart is exposed and a larger number of sites are to be stabilized. As described hereinabove, the motion sensor signals serve as feedback to enable the control unit to modify pulses applied to the heart, in order to reduce the detected motion of the segment. Additionally or alternatively, local sense electrodes 74, which optionally comprise some or all of electrodes 100, convey electrical signals to control unit 90 to enable parameter search and tuning block 84 to synchronize the electrical signals generated by electrodes 100 with the natural electrical activity of the heart and with propagation characteristics of the applied signals.

In a preferred embodiment of the present invention, some of electrodes 100 apply rapid pulses to segment 24 which are generally similar in form and intensity to pulses used to pace the heart. The pulses induce a reversible state of generally constant contraction of the segment, without causing fibrillation or other dangerous arrhythmic activity. In a preferred rapid-pacing mode, control unit 90 generates a regularly-spaced series of current pulses, injecting current through the electrodes into underlying cardiac tissue. In this mode, the pulses are preferably characterized by a frequency above 5 Hz, and are typically applied above 10 Hz. Pulses applied between about 25 and 30 Hz have generally been shown to produce desirable results. Other parameters typically characterizing the pulses include a duty cycle between about 5 and 50%, a DC offset between about −10 and +10 mA, and an amplitude between about −20 and +20 mA. An amplitude of between about 1 and 5 mA is typically sufficient. These values are cited by way of example, however, and it will be understood that higher or lower frequencies and amplitudes may also be used, depending on the type and placement of the electrodes and on the specific condition of the patient's heart. For example, a frequency higher than 100 Hz was tested on rabbits and found to yield suitable results.

In another preferred embodiment of the present invention, control unit 90 applies a fencing signal to some of electrodes 100, generally in order to inhibit the generation and propagation of an action potential from one region of the heart to another. Fencing is typically used in these applications to block or reduce the normal propagation of signals and/or to reduce the contractility of affected muscle tissue. Even to the extent that fencing does not completely block propagation of activation signals, the fencing generally reduces the strength of the resultant muscle contraction. Segment 24 and/or other areas of the heart are stimulated, as described hereinabove, to contract in a manner that roughly cancels out the effect of global heart motion, so that the segment is held generally still during surgery. When fencing of segment 24 is applied during calibration and operation of apparatus 18, it typically allows muscle contractions within segment 24 to be controllable by control unit 90 substantially independently of the natural electrical activity of the heart.

In general, each one of electrodes 100 conveys a particular waveform to heart 20, differing in certain aspects from the waveforms applied by the other electrodes. The particular waveform to be applied is determined by control unit 90, preferably under the control of a human operator Aspects of the waveforms which are set by the control unit, and may differ from electrode to electrode, typically comprise parameters such as time shifts between application of waveforms at different electrodes, waveform shapes, amplitudes, DC offsets, durations, frequencies, duty cycles, etc. For example, although the waveforms applied to the electrodes typically comprise a series of monophasic square wave pacing pulses, other waveforms, such as a sinusoid, a series of uniphasic and/or biphasic square waves, or substantially any other shape known in the art of applying electric signals to tissue, could be used in the framework of the present invention. Additionally, in some operational modes, the voltage applied by some or all of electrodes 100 is controlled, rather than the current, as described hereinabove.

Generally, the shape, magnitude, and timing of the waveforms are optimized for each patient, using suitable optimization algorithms, as are known in the art, in order to attain a desired level of stabilization of segment 24. Typically, the optimization is performed continually, both during the calibration period and during regular operation. However, during a surgical procedure, the operational parameters are typically changed more gradually, so as not to interrupt the surgeon's actions.

Preferably, application of the electrical signals in accordance with the present invention stabilizes segment 24 within a very short period (e.g., several seconds), and can maintain the segment's stability for prolonged periods, (e.g., at least several minutes) The heart typically returns to normal function within about 2 seconds of removal of the electrical signals. A short waiting time, typically about 15 seconds, is preferably followed by recalibration before signals are applied again. Although the initial calibration period can take several minutes in order to determine appropriate signals to be applied by electrodes 100, recalibration typically requires less time. The method of the present invention does not harm the heart tissue and is spontaneously reversible, generally without requiring cardioversion or defibrillation. (Cardioversion and defibrillation capabilities are nevertheless typically provided to enhance safety.)

Although preferred embodiments are described hereinabove with reference to reducing motion of the segment of the heart in order to enable surgery on the segment, it will be understood that the present invention may be used for other purposes, such as to enhance a physician's ability to perform diagnostic tests on the segment. Furthermore, the principles of the present invention are applicable not only to the heart, but also to controlling local motion in segments of other types of tissue, such as the intestines and other smooth, as well as skeletal, muscle.

It will further be appreciated that the individual preferred embodiments described above are cited by way of example, and that specific applications of the present invention will typically employ features described with reference to a plurality of the figures. The full scope of the invention is limited only by the claims.

What is claimed is:

1. A method for performing a medical procedure on a beating heart, comprising:
    applying electrical signals to the heart so as to reduce motion of a segment thereof;
    performing the procedure while the heart continues to pump blood; and
    mechanically stabilizing the segment in conjunction with applying the electrical signals.

2. A method for performing a medical procedure on a beating heart, comprising:
    applying electrical signals to the heart so as to reduce motion of a segment thereof; and
    performing the procedure while the heart continues to pump blood,
        wherein applying the electrical signals comprises calibrating the signals intermittently during the procedure.

3. A method for performing a medical procedure on a beating heart, comprising:
    applying electrical signals to the heart so as to reduce motion of a segment thereof; and
    performing the procedure while the heart continues to pump blood,
        wherein applying the electrical signals comprises applying a first signal so as to precondition a response of the heart to a subsequent signal, which reduces the motion during the procedure.

4. A method for performing a medical procedure on a beating heart, comprising:

applying electrical signals to the heart so as to reduce motion of a segment thereof;

performing the procedure while the heart continues to pump blood; and sensing motion of the heart, wherein applying the signals comprises modifying a characteristic of at least some of the signals applied to the heart responsive to the sensed motion.

5. A method according to claim 4, wherein sensing the motion comprises coupling at least one motion sensor to detect motion of the segment of the heart, wherein modifying the characteristic comprises modifying a signal characteristic so as to reduce the motion of the segment.

6. A method for performing a medical procedure on a beating heart, comprising:

applying electrical signals to the heart so as to reduce motion of a segment thereof; and performing the procedure while the heart continues to pump blood, wherein applying the electrical signals comprises applying signals at a plurality of sites on the heart, and wherein applying the signals comprises applying a first waveform at a first one of the sites and applying a second waveform, which differs from the first waveform, at a second one of the sites.

7. A method according to claim 6, wherein applying the first and second waveforms comprises controlling a timing relationship of the waveforms so as to reduce the motion of the segment.

8. Apparatus for performing a medical procedure on a beating heart, comprising:

one or more electrodes, coupled to the heart;

a control unit, which actuates the electrodes to apply electrical signals to the heart so as to substantially reduce motion of a segment thereof while the heart continues to pump blood, whereby the procedure is performed on the segment; and one or more motion sensors, coupled to the heart and to the control unit, which sense motion of the heart, wherein the control unit modifies the signals applied to the heart responsive to the motion.

9. Apparatus according to claim 8, wherein at least one of the one or more motion sensors is coupled to the segment of the heart, and wherein the control unit modifies the signals so as to minimize motion sensed by the at least one sensor.

10. Apparatus for performing a medical procedure on a beating heart, comprising:

one or more electrodes, coupled to the heart;

a control unit, which actuates the electrodes to apply electrical signals to the heart so as to substantially reduce motion of a segment thereof while the heart continues to pump blood, whereby the procedure is performed on the segment; and one or more fencing electrodes, coupled to the heart, which are actuated by the control unit to apply a fencing signal to the heart so as to block propagation of an activation wave into the segment.

11. Apparatus for performing a medical procedure on a beating heart, comprising:

one or more electrodes, coupled to the heart; and a control unit, which actuates the electrodes to apply electrical signals to the heart so as to substantially reduce motion of a segment thereof while the heart continues to pump blood, whereby the procedure is performed on the segment; and one or more fencing electrodes, coupled to heart tissue in a vicinity of the segment, which are actuated by the control unit to apply a fencing signal to the segment so as to reduce a contraction force thereof.

12. Apparatus for performing a medical procedure on a beating heart, comprising:

one or more electrodes, coupled to the heart;

a control unit, which actuates the electrodes to apply electrical signals to the heart so as to substantially reduce motion of a segment thereof while the heart continues to pump blood, whereby the procedure is performed on the segment; and a mechanical stabilizer, which is applied to the heart to restrain motion thereof, in conjunction with motion reduction using the one or more electrodes.

13. A method for performing a medical procedure on smooth muscle tissue having a tendency to motion, comprising:

applying electrical signals to the tissue so as to reduce motion of a segment thereof, such that the motion increases spontaneously upon removal of the signals; and performing the procedure while the motion is reduced.

14. A method for performing a medical procedure on skeletal muscle tissue having a tendency to motion, comprising:

applying electrical signals to the tissue so as to reduce motion of a segment thereof, such that the motion increases spontaneously upon removal of the signals; and performing the procedure while the motion is reduced.

15. A method for performing a medical procedure on muscle tissue having a tendency to motion, comprising:

applying electrical signals to the tissue so as to reduce motion of a segment thereof, such that the motion increases spontaneously upon removal of the signals; and performing the procedure while the motion is reduced, wherein performing the procedure comprises performing a diagnostic procedure.

* * * * *